US007456291B2

(12) United States Patent
Valletta

(10) Patent No.: US 7,456,291 B2
(45) Date of Patent: *Nov. 25, 2008

(54) USE OF A VITAMIN COMBINATION FOR THE TREATMENT OF PRIMARY HEADACHES

(76) Inventor: Giampiero Valletta, Via Campidoglio, 188, Ceprano (IT) 03024

( * ) Notice: Subject to any disclaimer, the term of this patent is extended or adjusted under 35 U.S.C. 154(b) by 0 days.

This patent is subject to a terminal disclaimer.

(21) Appl. No.: 10/343,853

(22) PCT Filed: Jul. 20, 2001

(86) PCT No.: PCT/IT01/00388

§ 371 (c)(1),
(2), (4) Date: Feb. 5, 2003

(87) PCT Pub. No.: WO02/11731

PCT Pub. Date: Feb. 14, 2002

(65) Prior Publication Data

US 2003/0181459 A1  Sep. 25, 2003

(30) Foreign Application Priority Data

Aug. 7, 2000 (IT) .......................... RM2000A0448

(51) Int. Cl.
*C07D 211/72* (2006.01)
*C07D 211/78* (2006.01)
*C07D 213/80* (2006.01)
*C07D 239/00* (2006.01)
*A01N 43/60* (2006.01)

(52) U.S. Cl. ........................ 546/317; 546/318; 546/319; 546/320; 544/251; 514/251

(58) Field of Classification Search ................. 514/251, 514/356
See application file for complete search history.

(56) References Cited

U.S. PATENT DOCUMENTS 2,480,517 A   8/1949  Stecher
3,478,041 A * 11/1969 Busing et al. ............... 546/318
4,973,467 A * 11/1990 Sahley ......................... 424/439
5,571,441 A * 11/1996 Andon et al. .................. 252/1
6,017,946 A    1/2000  Posner
6,159,505 A * 12/2000 Piper ........................... 424/679

FOREIGN PATENT DOCUMENTS

| WO | WO 97/26897 | 7/1997 |
| WO | WO 99/66943 | 12/1999 |
| WO | WO 00/69426 | 11/2000 |

OTHER PUBLICATIONS

Schoenen et al., Cephalalgia, 1994;14(5):328-329.*
Smith, Clifford. The Role of Riboflavin in Migraine.1946.Canada M.A.J. p. 589-591 ).*
Fritton, Margarette. Uber die Behandlung der Migrane mit Nikotinsaureamide (Therapy of Migraine with Nicotinic Acid Amide).Sep. 17, 1955 (38).p. 1350-1.*
Atkinson (Headache: The Journal of Head and Face Pain; Migraine and Meniere's Disease; vol. 2 Issue 2;Jul. 1962;p. 109-119).*
Ogden HD et al. "Clinical study of headache relief with a niacin-containing compound", Headache 1962, 1, pp. 21-29.
J. Schoenen et al., "High-Dose Riboflavin as a Prophylactic Treatment of Migraine: results of an open pilot study", Cephalalgia, Scandinavian Press, NO, vol. 14, No. 5, 1994, pp. 328-329.

* cited by examiner

*Primary Examiner*—Sreeni Padmanabhan
*Assistant Examiner*—Layla Soroush
(74) *Attorney, Agent, or Firm*—Young & Thompson

(57) ABSTRACT

Use of a combination of two vitamin compounds, i.e. riboflavin (also known as vitamin $B_2$) and nicotinic acid (also referred to as niacin) or, as an alternative thereto, the corresponding amide, i.e. niacinamide or nicotinamide (also known as vitamin PP) for the treatment of various forms of primary headache, such as classical migraine or migraine with an aura, common migraine or migraine without an aura, complicated migraine and cluster headache or histamine headache. The invention also concerns compositions for the treatment of primary headaches which are based on the two aforesaid active ingredients.

6 Claims, No Drawings

USE OF A VITAMIN COMBINATION FOR THE TREATMENT OF PRIMARY HEADACHES

The present invention concerns the use of a vitamin combination for the treatment of primary headaches. More particularly, this invention relates to the use of a combination of two vitamin compounds, i.e. riboflavin (also known as vitamin $B_2$) and nicotinic acid (also referred to as niacin) or, as an alternative thereto, the corresponding amide,. i.e. niacinamide or nicotinamide (also known as vitamin PP) for the treatment of various forms of primary, headaches, among which common migraine, classical migraine or migraine with aura, duster headache and complicated migraine.

BACKGROUND OF THE INVENTION

As it is known, the term headache is currently taken to mean any form of more or less intense pain localised in the head. This pain may have various origins and in only about 10% of the cases it is caused by a specific organic illness, Under this profile it is possible to distinguish primitive or primary headaches, the cause of which is not accurately identifiable, and secondary headaches, which always constitute the symptom of another primary disorder, Examples of secondary headaches include sinusitis, headache due to cerebral hemorrhage, headache due to endocranial hypertension (in particular, caused by brain tumors), headache caused by infective meningitis and headache due to arterial hypertension. In all cases, the diagnosis calls for an accurate examination that not only takes the pain characteristics into account, but also the familiarity and relations with other disorders, causal factors and reactions to various pharmaceuticals, and in most cases requires a series of tests such as a blood test, X-rays of the cranium and cervical column, EEG and echography, Once having excluded that the symptoms are linked to a different basic disorder, then it is likely that the disorder is one of the possible arms of primary headaches, often referred to as a "migraine", which affect about 20-30% of the population (prevalently women). According to one of the current classifications, this may be of one of the following four forms: 1) classical migraine, i.e. with an aura; 2) common migraine, i.e. without an aura; 3) complicated migraine; 4) cluster headache.

Apart from the cluster headache, the aforesaid other forms of migraine generally consist of a pulsating periodic headache affecting one half of the cranium, and often associated with nausea and/or vomiting. The disorder generally starts in childhood, during adolescence and early adulthood and decreases in intensity and frequency over the years. In particular, a classical migraine starts with the so-called aura, consisting of protracted neurological symptoms for 30 minutes and includes photophobia, flashing scotoma (ie. bright flashing sensations before the eyes, with jagged edging similar to a wall), vertigo and tinnitus. With common migraines the headache arise with-out a prior aura, but often involves nausea or vomiting. Complicated migraines are instead characterised by headaches associated with particular neurological symptoms that may precede or accompany them. In particular, there may be paresthesia and hypoesthesia of the lips, face, hand and leg of al hemi-soma, sometimes associated with aphasic disorders, or one end of an arm or leg may become hyposthenic or plegic simulating an ictus. The sensitive disorders or feelings of weakness extend slowly from one side of the body to the other for a period a few minutes. Usually, after an attack, there in a complete return to normality, but there may also be permanent deficiencies among which hemianopsia, hemiplegia and hemianestesia. Cluster headache, also referred to as paroxysmal nocturnal headache, hemicranial neuralgia, histamine headache and Horton's syndrome, is four times more common in men than in women, and is characterised by a constant unilateral orbital pain generally beginning two or three hours after sleep onset. The pain is intense and steady but not pulsating, and involves lachrymation, nasal congestion, rhinorrhea and then myosis, reddening and oadema of the cheek that lasts for about 30 an hour. This form of headache tends to occur cyclically during the right for several weeks or months (hence the name "cluster") and is then followed by a complete recovery for months or even years. Episodes of cluster headache of 2-3 week duration may arise several times in a lifetime.

The physiopathological mechanisms of the various forms of primary headache have been the subject of many studies and to date no pathogenetic theory that appears satisfactory to all researchers has been proposed. Many factors have been put forward as possible causes of a migraine attack, among which stress, physical strain, the weather, hormone fluctuations, bright lights and the intake of certain foods or beverages, such as those containing caffeine or alcohol. In any case, the migraine symptoms are always associated with variations in cerebral blood flow, presumably as a result of changes in blood vessel dimensions: normally, the prodromes are accompanied by arterial constriction and a reduction in cerebral blood flow, and are followed by blood vessel dilation corresponding to the actual headache onset. However, the factors which determine these changes in cerebral blood flow and the mechanisms through which such changes are linked to pain are controversial. One of the hypotheses claims that a migraine is due to a neurovascular disorder of the central nervous system (in particular, of the hypothalamus and brainstem) which involves alterations in vasomotor regulation, while another hypothesis interprets the disorder as a systemic metabolic imbalance with attacks caused by intravascular factors associated with serotonin (or 5-hydroxytriptamine, 5-HT) variations in the metabolism. It has been found, though, that migraines are accompanied by variations in platelet serotonin levels with a fall in these levels, during a migraine attack, due to the release —associated with increased urinary excretion —of its main metabolite, 5-hydroxyindolacetic acid.

According to some more recent observations, during a migraine attack there is an overflow of plasmatic proteins and the development of localised inflammation of intracranial blood vessels, together with the activation of trigeminal innervation of cerebral blood circulation. This phenomenon also sees the action of certain peptidic neurotransmitters which have a vasodilatory effect and are contained in the nerve fibres of the trigeminovascular system, in particular the CGRP (calcitonin gene-related peptide) and SP (substance P). These neurotransmitters appear to be particularly important in pain transmission and they are thought to be also involved in local tissue reactions of an inflammatory type. In particular, it has been demonstrated that substance P causes protein overflow and the typical inflammatory reaction triggered by the degranulation of mastocytes even in the brain dura mater, the connective tissue covering and protecting the brain matter, and which contains the cerebral blood vessels and their accompanying nerve fibres (Moskowitz M. A., Basic mechanisms in vascular headache, *Neual. Clin.* 8:801-415, 1990; Moskowitz M. A. and Outrer F. M., Sumatripan, a receptor-tareted treatment of migraine, Ann. Revs Med., 44:145-154, 1993; May A., Goadsby P. J., The Trigeminovascular System in Humans: Pathophysiological Implications for Primary Headache Syndromes of the Neural Influences on the Cerebral Circulation, J. Cereb. Blood Flow Metab., 19:115-117, 1999).

As well as the two aforesaid vasodilating neurotransmitters and serotonin, other chemical agents seem to be involved, depending on the cases, in causing headache pain, such as histamine (as the term histamine headaches attributed to the cluster headache implies), thromboxan $A_2$, prostaglandins and quinines. Current migraine treatment partly takes these chemical agents into account with therapies that aim to neutralise their action. This is the case, for example, with anti-inflammatory drugs and analgesics currently used in particular cases of headache. Other currently used treatments are ergotamine and its derivatives; ergot alkaloids that appear to be mostly active against classical and common migraines, and only if taken early during an attack; metisergide, an antiserotoninegic drug (a strong antagonist of 5-$HT_1$ receptors), especially useful as a preventive measure; and the selective agonists of the 5-$HT_1$ receptors, above all, sumatryptan. The latter can trigger 5-$HT_1$ serotonin receptors which mediate localised vasoconstriction at the carotid level, thereby reducing blood flow to the extra and intracranial tissues. Although effective in reducing the headache pain symptom, these products are not devoid of side-effects Moreover, to develop a quick response they need to be administered by subcutaneous injection.

SUMMARY OF THE INVENTION

An object of the present invention is therefore to provide a consistently effective pharmacological therapy, that is easy to administer and devoid of harmful side-effects, suitable for the successful resolution of various forms of primary headache that have hitherto been unsatisfactorily treated or unresolved. To achieve such purpose, in the frame of the research leading to the present invention a particular vitamin combination has been taken into consideration, composed of nicotinic or 3-pyridincarboxylic acid, also known as niacin (or, in alternative thereto, nicotinamide, also referred to as vitamin PP) and riboflavin (also known as vitamin $B_2$).

The first ingredient of the aforesaid combination, nicotinic acid, is a well-known vitamin factor commonly found in a great many vegetable and animal tissues, and particularly in food sources such as meat, poultry, fish, liver, kidney, eggs, nuts, butter, milk and yeast. In human beings, nicotinic acid may also be synthesised from the amino acid tryptophan, but the latter source is normally insufficient to meet the dietary requirements for this vitamin. In fact, the alternative name of vitamin PP (or P.P. factor, i.e. pellagra preventive factor) that is commonly used is due to its critical activity in the prevention of pellagra. The latter is a disease caused by vitamin deficiency, that occurs in dietary regimens poor in tryptophan (or, correspondingly, niacin or nicotinamide), such as a diet mainly based on maize and with very little animal protein intake.

Nicotinic acid functions in the body only after it has been converted into one or the other of the physiologically active forms —nicotinamide adenine dinucleotide (NAD) or nicotinamide adenine dinucleotide phosphate (NADP). These serve as coenzymes for a wide variety of proteins that catalyse oxidation-reduction reactions essential for tissue respiration. This biological process is the result of several oxidation-reduction reactions occurring within the cells, in particular in the mitochondria, in order to oxidise that part of material reaching the cells (through the bloodstream) so as to be used for energy production. Among the various enzymes responsible for oxidative processes (oxidoreductases), that perform their function by accepting a $H_2$ molecule from the substrate, the enzymes known as dehydrogenases cannot use molecular oxygen as an immediate acceptor of the hydrogen taken from the substrate, but have to use the pyridine coenzymes (NAD and NADP) as acceptors. Hence, the presence of these coenzymes is vitally important for the proper development of the biochemical cycles that produce energy, such as from sugars (glycolysis and Krebs cycle) and from fatty acids (beta-oxidation), or in the metabolic pathway leading to urea (ornithine cycle).

In view of the above, the presence of adequate levels of nicotinic acid and/or nicotinamide (or tryptophan) in the body is an essential requirement for the regular functioning of the gastrointestinal tract, for a healthy skin, for nervous system maintenance and for the synthesis of the sex hormones. Symptoms of deficiency may be muscular weakness, generalised asthenia, loss of appetite, cutaneous eruptions, stomatites, insomnia, nausea and migraine. As recalled above, severe deficiencies lead to pellagra. The doses of nicotinic acid, nicotinamide or of suitable derivatives (such as methyl nicotinate) normally used for treating pellagra are of about 50 mg, by the oral route, up to 10 times a day. If oral administration is not possible, then intravenous injections of 25 mg of the vitamin may be administered twice a day.

It is also well-known that nicotinic acid and nicotinamide are effective in improving blood circulation and in lowering cholesterol levels. As regards the first effect, some products for the topical administration containing nicotinic acid are available, having the function of a topical rubefacient and analgesic, for the relief of muscular pain and rheumatism. In these products, niacin assumedly enhances the peripheral blood circulation since it dilates subcutaneous blood vessels after penetrating the skin.

As regards the second effect mentioned above, niacin is used in systemic administration, i.e. by the oral or parenteral route, at higher doses than those mentioned above for the prophylaxis and treatment of pellagra (i.e. 2-6 g per day) in preparations for hyperlipidemia therapy, for lowering cholesterol levels in the blood. However, at the high systemic doses required by this treatment, both nicotininc acid and nicotinamide have shown a certain number of adverse side-effects, including gastrointestinal reactions (abdominal pain and nausea), hepatotoxicity and, above all, flushing (cutaneous erythema) often accompanied by warmth, tingling and itching.

In order to reduce these side-effects while maintaining the doses required for antilipemic treatment, changes have been proposed for the nicotinic acid molecule by creating various derivatives as well as combinations of niacin or nicotinarnide with other active ingredients or adjuvants, and particular formulations and dosages. Examples of these variants are described in the European patent application EP-A-0349235 (and the corresponding U.S. Pat. No. 4,965,252), concerning an antihyperlipidemic composition based on nicotinic acid for oral administration where the undesired side-effects of the active ingredient are eliminated by mixing with guar gum, and in the international patent publication WO-A-9632942, concerning a combination of a therapeutically effective amount of methyl nicotinate and a non-steroidal anti-inflammatory drug (NSAID), preferably in a sustained release form, in the aim of reducing the irritating action characterising niacin when used as an antihyperlipemic agent.

Within the studies leading to the present invention, in the first phase it was checked that, while the systemic administration of nicotinic acid or nicotinamide in doses well below those employed for the treatment of hypercholesterolemy—i.e. the typical dosage used when using the same agents for the prevention and treatment of pellagra—does not lead to the secondary reactions that have been reported for high doses, nevertheless it is not very effective in combating the forms of headache considered by this invention. Actually, according to the clinical experimentation carried out and reported in part further on, neither the common migraine, classical migraine and the so-called complicated migraine, nor the cluster headache have appeared to satisfactorily respond to drugs based on only nicotinamide or on only nicotinic acid. On the other hand, the desired effect is obtained when niacin or nicotinamide are administered systemically in a combination with another known vitamin agent, i.e. riboflavin or vitamin $B_2$.

This second active ingredient, having chemical name 7,8-dimethyl-10(D-ribo-2,3,4,5-tetrahydroxypenthyl)isoalloxazine, is itself also a nutritional factor of primary importance that is mainly found in milk, eggs, cheese, liver, heart, kidney and green vegetables. Riboflavin performs its own biological functions in the body in the form of an essential component of two coenzymes, riboflavin phosphate, commonly known as flavin mononucleotide (FMN) and flavin adenin dinucleotide (FAD).The latter two coenzymes, like the two aforesaid pyridine enzymes (i.e. NAD and NADP), cooperate with respiratory flavo-proteins in oxidising the substrate by accepting a hydrogen molecule from it s but, unlike NAD and NAOP, may release the hydrogen molecule directly to the molecular oxygen. Moreover, the oxidation-reduction potential of FMN and FAD is such that these two compounds are able to oxidise the reduced pyridine coenzymes. In fact the function of flavoproteins (of which, as already mentioned, FMN and FAD constitute the coenzymes) is, on the one hand, to directly oxidise the substrates and, on the other, to contribute to pyridine cenzyme functioning by re-oxidising them once the latter have been reduced after interacting with a substrate.

DETAILED DESCRIPTION OF THE INVENTION

In view of the above and considering that in practice the pyridine co-enzymes (NAD and NAL)P) can perform their function only in the presence of flavo-proteins, i.e. of riboflavin, it may be seen how the presence of both these agents is necessary for the correct functioning of the biochemical mechanisms governing cell metabolism, Without wishing to be bound by any particular theory concerning the mechanism of action of the proposed combination of active ingredients, it is considered that both niacin and riboflavin play a crucial role in the metabolism of mastocytes. A deficiency of either of these agents would adversely affect the energy production phase of the metabolic chain that leads to the activation of these calls, that is mainly responsible for releasing the biochemical mediators and neurotransmitters mentioned above. As is known, mastocytes or mast cells are found in organs rich in connective tissue, such as the shin and the respiratory and gastrointestinal tracts and—as regards those aspects concerning the present invention—the cerebral dura mater, and are characterised by the presence of granules which may be secreted by the mast cell following its activation, in this way releasing the various mediators and neurotransmitters mentioned above.

According to the present invention, it has been considered that once the mastocytes are activated then a series of enzymatic reactions take place in the cell that include an energy-requiring phase and terminate wit the de-granulation of the mastocyte and the release of preformed or newly synthesised mediators. In view of the results of the clinical trials presented below It is reasonable to hypothesise that migraine or cluster headache pain is caused by an energy-controlled alteration in the metabolic mechanism leading to the mastocytic secretion of the mentioned biochemical mediators and neurotransmitters, and that the systemic administration of a suitable dose of niacin or nicotinamide together with riboflavin will provide the body with the necessary NAD/NADP and FAD/FMN in order to appropriately modulate the activity of these cells With specific reference to migraines, and particularly to instances linked to premenstrual syndrome such as pain, depression, migraine and fatigue, the international patent publication WO-A-9917612 suggests using a formulation based on serotonin, probably starting from the already reported idea of the drop in serotonin levels during a migraine. According to this document. the proposal of administering serotonin for treating various problems including headaches had already been put forward, but oral administration was considered impossible due to the oxidising degradation of this active ingredient in the gastrointestinal tract. This meant that it was necessary to use a precursor of serotonin instead of serotonin itself—L-tryptophan—for It to be converted into serotonin after administration. According to the publication at issue, on the contrary, the oral administration of an effective quantity of serotonin was suggested In combination with a suitable antioxidant (e.g. vitamin C or vitamin E), In order to prevent serotonin degradation in the gastrointestinal tract. The publication also suggested formulations in which the two mentioned agents are combined with adjuvants selected from within the broad group of vitamin factors and, among these, also riboflavin and niacin or nicotinarnde. It is worth noting that the specification exclusively attributes to serotonin dosed in a sufficient quantity to take the haematic level of this neurotransmitter above normal levels—a therapeutic action for the treatment of premenstrual syndrome. The experimental data presented show that the subjective symptoms of this disorder are depression, migraines and generic "premenstrual symptoms". In view of all the above, it is obvious that the formulation described in the publication concerned is not exploitable for a valid effective treatment of the primary headache forms considered here.

Accordingly, the present invention specifically provides the use of a combination of nicotinic acid or of nicotinamide with riboflavin for the production of a medicament for the treatment and/or the prophylaxis of primary headache forms. More specifically, this preparation is effective for the treatment and/or prophylaxis of common migraines, classical migraines, complicated migraines and cluster headaches.

For the therapeutic indications of the present invention, the two active ingredients must be administered systemically—particularly via the oral or parenteral route—using a dosage of between 0.5 and 750 mg per day of niacin or of nicotinamide, and between 0.1 and 250 mg per day of riboflavin. Preferably, this combination will include niacin or nicotinamide and riboflavin in a ratio between 40:1 and 10:1 (nicotinic acid or nicotinamide: riboflavin), while the best ratio is 20:1 (niacinamide: riboflavin). According to a particularly effective therapeutic protocol, 50 mg of nicotinamide+2.5 mg of riboflavin are administered orally twice a day, continuing the treatment until the migraine disappears. Then, in some particular cases, the treatment is continued for another short period and, if necessary, continuing with half doses of the vitamin combination for about another 15 days.

The compounds of the invention may be administered in different ways, for example via the oral or parenteral route. In such administrations, the two active ingredients may be incorporated in traditional pharmaceutical formulations in the form of solid or liquid dosages. These may contain the usual additives employed in pharmaceutical techniques such as, for example, sweeteners, flavourings, colourings, coverings and preservatives, inert diluents such as calcium carbonate, sodium carbonate, lactose and talc, binding agents such as amide, gelatine and polyvinylpyrrolidone, suspending agents such as methyl cellulose or hydroxyethyl cellulose and inhibitors such as lecithin, polyoxyethylene stearate and polyoxyethylene sorbitan monooleate, reducing agents such as ascorbic acid and its salts. The formulations for parenteral administration (more specifically, to be injected intravenously or intra muscularly) may also contain the active ingredients dissolved or suspended in distilled water, together with the most common pharmaceutically acceptable excipients.

A particularly effective therapeutic protocol for the treatment of various forms of headache is the following. $1^{st}$ phase: 50 mg of nicotinamide+2.5 mg of riboflavin twice a day until the headache disappears; then continue with 50 mg of nicotinamide+2.5 mg of riboflavin per day for 15 days; $2^{nd}$ phase (optional): 50 mg of nicotinamide+2.5 mg of riboflavin per day for 15 days a month for the prophylaxis. It is advisable to take the compounds via the oral route, after the main meals, with abundant water (at least half a glass). In cases where pain returns after suspending the treatment, it will be necessary to start from the $1^{st}$ phase again.

As already noted, alternatively to oral administration it is also possible to use injections, with a preferred dosage of 20 mg of nicotinamide+1 mg of riboflavin once or twice a day.

According to a further specific aspect, the present invention also concerns a composition for the treatment and/or prophylaxis of primary headaches using as active ingredients a combination of nicotinic acid or nicotinamide and riboflavin. The particularly preferred characteristics of these compositions are provided in the attached claims. It is obvious, however, that the two active ingredients of the invention must not necessarily be contained in the same product, since it is also possible to administer them separately as long as the dosage and therapeutic protocol are the ones illustrated above.

Some experimental results obtained according to the present invention, including clinical data on the performance of the proposed combination in comparison with the use of nicotinic acid or nicotinamide alone, are reported below for merely illustrative purposes.

$1^{st}$ Series of Tests—Treatment with the Nicotinamide-Riboflavin Combination $1^{st}$ case—a 49-year-old woman with a classical migraine (or a migraine with an aura). The patient had been suffering from classical migraine symptoms for 30 years. Initially, the symptoms were located in the right temporal region and later spread to the top and to the left temple with characteristic pulsations, accompanied by photophobia, vertigo and buzzing ears. The attacks lasted for about 10 days on a monthly basis. She had been undergoing treatment for a certain period at the Cephalalgia Unit of Florence University, where her therapy was based on vasoconstrictors (ergotamines) and anti-inflammatory analgesics, which were not successful.

Later, during a migraine attack, the patient started a treatment based on 50 mg of nicotinamide+2.5 mg of riboflavin taken orally twice a day. Just two days into the treatment the symptoms were greatly reduced and they completely disappeared on the third day. During this period the patient had completely suspended the old therapy. She continued with the new treatment, according to the present invention, for another 7 days to then temporarily suspend it. Later on, the dosage was halved for 10 days a month for preventive purposes. In the next 4 months from starting the treatment, the patient no longer had any migraine attacks.

$2^{nd}$ case—a 25-year-old woman with a common migraine (or a migraine without an aura). The patient suffered from a common migraine starting on the right side with the pulsating characteristic and accompanied by nausea.

The problem had been diagnosed about 9 years before at a neurology department of Rome's "La Sapienza" University. Since then she had taken analgesics and vasoconstrictors for about 8 consecutive days every two weeks, but benefited little from them.

Later, on medical advice, at the onset of a migraine attack the patient started taking 50 mg of nicotinamide+2.5 mg of riboflavin orally twice a day. After two days the pain dropped and then disappeared. She continued treatment for another 10 days with this protocol and then the dosage was halved.

In the next 6 months from the start of the treatment she had no further migraine attacks.

$3^{rd}$ case —a 36-year-old woman with complicated migraine. The patient had been suffering from complicated migraines since the age of 23 years.

She had undergone treatment at the Cephalalgia Unit of Rome's "La Sapienza" University with analgesics, anti-inflammatory ergotamines and, finally, also anti-serotoninergic drugs. These treatments not only led to very slight improvements, but even brought on considerable adverse side-effects such as myalgia, neck and limb pains, and asthenia. Before starting the treatment of the present invention, the patient had a right-side hemicranial pain with photophobia, buzzing ears and left hemisoma motility disorders.

She was prescribed a therapy based on 50 mg of nicotinamide+2.5 mg of riboflavin taken orally twice a day. After 3 days the symptoms were greatly reduced and then disappeared completely on the fifth day. The patient continued to follow the same treatment for another 15 days and then went on a 15-day treatment every month with half the dosage. After 7 months from the start of treatment the check-ups every 15 days showed the absence of any migraine attacks.

$4^{th}$ case—a 32-year-old man with cluster headaches. The patient had been suffering from nocturnal headaches for about 15 years. The headaches started about 3 hours after sleep onset and presented a left orbital pain, lachrymation, nasal congestion and an oedema of the left cheek. He had been treated from the start of the symptoms at the Cephalalgia Unit of Rome's "La Sapienza" University, where a cluster headache (or histamine headache or Horton's syndrome) was diagnosed. The treatment consisted of ergotamines and antidepressants which only gave very slight relief.

The patient was thus treated with 50 mg of nicotinamide+ 2.5 mg of riboflavin taken orally twice a day After 3 days the nocturnal headache symptoms completely disappeared. He continued with the therapy for another 15 days and then the dosage was halved and treatment continued for 15 days a month. In the next 19 months of observation he had no further cluster headache episodes.

$2^{nd}$ Series of Tests—Treatment in Two Phases: First with only Nicotinamide and then with the Nicotinamide-Riboflavin Combination $1^{st}$ case—a 35-year-old woman with a classical migraine (or migraine with an aura). The patient had been suffering from classical migraine symptoms for 15 years and had photophobia, flashing scotoma and vertigo. The problem had been diagnosed at the at the Cephalalgia Unit of Rome's "La Sapienza" University, where she was prescribed a treatment based on ergotamines, analgesic and anti-inflammatory drugs which were not very successful. The symptoms were located on the right side, occurred about twice a month and lasted a week, on average. When suffering from migraines the patient could not perform any activity. The acute episodes were preceded by photophobia, buzzing ears and visual disorders (scotoma).

During a migraine attack the patient had started taking 50 mg of nicotinamide orally twice a day and the migraine symptoms attenuated after 5 days but did not disappear completely. She continued with the treatment and after about 10 days the migraine returned, even if of a lesser intensity. The patient was then treated with 50 mg of nicotinamide+2.5 mg of riboflavin taken orally twice a day and the migraine disappeared after 3 days. She continued with the vitamin combination for another 15 days and then switched to taking the vitamin combination just once a day for 15 days a month. After 6 months from starting the treatment, the patient no longer had any migraine attacks.

$2^{nd}$ case—a 32-year-old man with complicated migraine. The patient had been suffering from complicated migraines since the age of 25 years. The symptoms were a pulsating type migraine localised on the right and preceded by photophobia and flashing scotoma. During migraine attacks he at times also had hyposthenia and a reduced sensibility of the left arm and leg. These symptoms arose about twice a month. He had initially undergone treatment at the Cephalalgia Unit of Rome's Gemelli Hospital with anti-inflammatory and ergotamine drugs and later also anti-serotoninergic drugs. These treatments only led to very slight improvements.

Thus, during a migraine attack, the patient started treatment based on 50 mg of nicotinamide taken orally twice a day and the problem was attenuated after 6 days. After adding 2.5 mg of riboflavin, taken orally twice a day, to the above therapy every symptom disappeared after another 2 days. The patient continued to take the two-vitamin combination at half dosage for 15 days a month. A check-up one year after starting the treatment revealed that he no longer had any migraine attacks.

$3^{rd}$ case—a 32-year-old woman with a common migraine. The patient had been suffering from the disorder for 15 years and the migraine occurred on the left side, accompanied by nausea. The painful episodes occurred every 15 days, on average. After being told she had a common migraine, she started treatment at the Cephalalgia Unit of Florence University. She was treated with anti-inflammatory, analgesic and ergotamine drugs and later also with anti-serotoninergic drugs, but had little relief from them.

The patient was then treated with 50 mg of nicotinamide taken orally twice a day and the migraine was partially attenuated in about 5 days. In a later check-up she was prescribed 2.5 mg of riboflavin taken orally twice a day in addition to the nicotinamide, and the migraine disappeared in another 2 days. The patient continued the same treatment for another 15 days and then the dosage was halved for 15 days a month. In the next 16 months from the start of the treatment she had no further migraine attacks.

$4^{th}$ case—a 42-year-old man with cluster headaches. The patient suffered from cluster headaches that made him wake up in the night with lacerating head pains. The pains were accompanied by lachrymation and rhinorrhea. The diagnosis had been made 20 years earlier at the Cephalalgia Unit of Rome's "La Sapienza" University and he had received treatment with ergotamines and antidepressants which only gave very slight relief.

The patient thus started treatment with 50 mg of nicotinamide taken orally twice a day and the headaches attenuated after 5-6 days. Later, 2.5 mg of riboflavin were also added to the treatment with nicotinamide and the headaches completely disappeared after 2 days. He continued to take 50 mg of nicotinamide and 2.5 mg of riboflavin orally per day for 15 days a month In the next 20 months of follow-up he had no further cluster headache episodes.

The foregoing experimental report clearly shows the superior effectiveness of the vitamin combination proposed in the present invention for the treatment of various forms of primary headaches, both in comparison with similar treatments suggested by the prior art and with those based on nicotinamide or niacin only.

The present invention has been disclosed with particular reference to some specific embodiments thereof, but it should be understood that modifications and changes may be made by the persons skilled in the art without departing from the scope of the invention as defined in the appended claims.

The invention claimed is:

1. A method for the treatment of a migraine or cluster headache in a subject in need of the same, said method consisting of administering to said subject a pharmaceutically acceptable vehicle or carrier, 0.5 to 750 mg of nicotinic acid or of nicotinamide, and 0.1 to 250 mg of riboflavin per day, in a ratio by weight of from 40:1 to 10:1 (nicotinic acid or nicotinamide: riboflavin).

2. The method according to claim 1, wherein said migraine headache is a migraine headache selected from the group consisting of common migraine, classic migraine, and complicated migraine.

3. The method according to claim 1, wherein said ratio by weight is 20:1.

4. The method according to claim 1, wherein the composition consists of 50 mg of nicotinic acid or nicotinamide and 2.5 mg of riboflavin.

5. The method according to claim 1, further comprising treating the headache until the headache disappears.

6. The method according to claim 5, further comprising treating the subject for another 15days with half dosages of the nicotinic acid or nicotinamide and riboflavin.

* * * * *